(12) United States Patent
Cagnon et al.

(10) Patent No.: US 7,279,572 B2
(45) Date of Patent: Oct. 9, 2007

(54) PROCESS FOR THE 2-STAGE SYNTHESIS OF HEXANITROHEXAAZAISOWURTZITANE STARTING FROM A PRIMARY AMINE

(75) Inventors: Guy Cagnon, Ballancourt (FR); Geneviève Eck, Monteux (FR); Grégoire Herve, Vert le Petit (FR); Guy Jacob, Vert le Petit (FR)

(73) Assignee: SNPE Materiaux Energetiques, Paris (FR)

( * ) Notice: Subject to any disclaimer, the term of this patent is extended or adjusted under 35 U.S.C. 154(b) by 368 days.

(21) Appl. No.: 10/833,025

(22) Filed: Apr. 28, 2004

(65) Prior Publication Data

US 2004/0260086 A1 Dec. 23, 2004

(30) Foreign Application Priority Data

May 22, 2003 (FR) .................................. 03 06160

(51) Int. Cl.
*C07D 487/00* (2006.01)
(52) U.S. Cl. ...................... 540/475; 540/554; 540/556; 149/92
(58) Field of Classification Search ................ 540/475, 540/554, 556; 149/92
See application file for complete search history.

(56) References Cited

U.S. PATENT DOCUMENTS 5,693,794 A 12/1997 Nielsen ...................... 540/554

6,147,209 A 11/2000 Wardle et al. .............. 540/556

FOREIGN PATENT DOCUMENTS

| EP | 0 753 519 A1 | 1/1997 |
| WO | WO 00/52011 | 9/2000 |

OTHER PUBLICATIONS

Nielsen, Arnold T. et al. "Polyazapolycyclics by Condensation of Aldehydes with Amines . . . " *Journal of Organic Chemistry*, 1990, pp. 1459-1966.
Surapaneni, Rao et al. "Process Improvements in CL-20 Manufacture." *Institut Chemische Technologie*, Jun. 27-30, 2000 pp. 108-1-108-4.

*Primary Examiner*—Brenda Coleman
(74) *Attorney, Agent, or Firm*—Oliff & Berridge, PLC

(57) ABSTRACT

A subject-matter of the present invention is a novel process for the synthesis of hexanitrohexaazaisowurtzitane (HNIW), a compound of use as energetic filler in powders, propellants and explosives.

This process comprises a first stage of reaction of an α,β-dicarbonyl derivative with a primary amine which makes it possible to form a hexasubstituted hexaazaisowurtzitane derivative.

The HNIW is subsequently obtained directly, in a single reaction stage, by nitration of the hexasubstituted hexaazaisowurtzitane derivative.

This process, in only 2 stages starting from a primary amine, is particularly simple and inexpensive.

13 Claims, No Drawings

PROCESS FOR THE 2-STAGE SYNTHESIS OF HEXANITROHEXAAZAISOWURTZITANE STARTING FROM A PRIMARY AMINE

The present invention relates to the field of powders for weapons, propellants and explosives which are very commonly used, in particular in the armaments industries.

A more specific subject-matter of the invention is a novel process for the synthesis of 2,4,6,8,10,12-hexa-nitro-2,4,6,8,10,12-hexaazatetracyclo[5.5.0.0$^{5,9}$.0$^{3,11}$]-dodecane, commonly referred to as hexanitrohexaazaisowurtzitane or HNIW.

It is known to use HNIW as energetic filler in powders, propellants and explosives, in particular as replacement for all or part of the octogen and hexogen. HNIW is currently the best performing energetic filler because of its high density and its high enthalpy of formation but the expansion of HNIW in replacing octogen and/or hexogen can only be envisaged if its production cost is significantly reduced.

This is because the processes for the synthesis of HNIW currently known are all very expensive.

U.S. Pat. No. 5,693,794 discloses, for example, the synthesis of HNIW in 4 stages starting from benzylamine and glyoxal.

In a first stage, 2,4,6,8,10,12-hexabenzyl-2,4,6,8,10,12-hexaazatetracyclo[5.5.0.0$^{5,9}$.0$^{3,11}$]-dodecane, commonly known as hexabenzylhexaazaisowurtzitane or HBIW, is obtained by reaction of benzylamine with glyoxal.

In a second stage, the HBIW is hydrogenolysed in hot acetic anhydride in the presence of a catalyst, which makes it possible to obtain 2,6,8,12-tetraacetyl-4,10-dibenzyl-2,4,6,8,10,12-hexaazaisowurtzitane, commonly known as tetraacetyldibenzylhexaazaisowurtzitane or TADBIW. The catalyst is very expensive and it is difficult to filter it off and to remove it.

In a third stage, the 2 benzyl groups of the TADBIW are replaced by nitroso groups, by reaction of the TADBIW with nitrosonium tetrafluoroborate, an expensive reagent, to form tetraacetyldinitrosohexaazaisowurtzitane (TADNIW).

In a fourth stage, the 4 acetyl groups and the 2 nitroso groups of the TADNIW are replaced to form HNIW by a nitrolysis reaction on the TADNIW with nitronium tetrafluoroborate, an expensive reagent.

This synthesis of HNIW in 4 stages starting from benzylamine and glyoxal is therefore particularly expensive, especially because of the large number of stages, long reaction times and high cost of the reagents.

Improvements in this process are known and consist mainly in eliminating the abovementioned third stage by replacing the TADBIW by an intermediate which can be nitrated directly, such as tetraacetylisowurtzitane (TAIW), tetraacetylmonoformylisowurtzitane (TAMFIW) or hexaacetylisowurtzitane (HAIW), which are obtained by carrying out the hydrogenolysis more exhaustively during the second stage. This exhaustive hydrogenolysis reaction on the HBIW has to be complete in order not to retain benzyl groups, which cannot be directly nitrolysed. This limitation requires an increase in the level of catalyst used for the hydrogenolysis and brings the cost of the TAIW, TAMFIW or HAIW to a value greater than that of the TADBIW, which limits the advantage resulting from the elimination of the third stage.

It is also known, during the final nitration stage, to replace the nitronium tetrafluoroborate by a less expensive sulphonic acid/nitric acid mixture.

U.S. Pat. No. 6,147,209, EP 753 519 and WO 00/52011, for example, disclose such improvements.

Despite these improvements, the cost of producing HNIW remains very high, essentially because of the 2 inescapable stages of synthesis of the HBIW intermediate and then of its hydrogenolysis in the presence of an expensive catalyst. This is why, for a very long time, the person skilled in the art has been looking for a new route for the synthesis of HNIW which would not be a simple improvement to the existing processes but which would be a different route which is simple, markedly less expensive, does not involve HBIW as intermediate compound and does not comprise an expensive stage of catalytic hydrogenolysis.

To our knowledge, no solution to this problem is described in the state of the art.

The present invention provides such a solution.

A subject-matter of the invention is a novel process for the synthesis of hexanitrohexaazaisowurtzitane comprising a first stage of reaction of an α,β-dicarbonyl derivative, preferably glyoxal, with a primary amine which makes it possible to form a 2,4,6,8,10,12-hexasubstituted-2,4,6,8,10,12-hexaazatetracyclo[5.5.0.0$^{5,9}$.0$^{3,11}$]dodecane derivative, subsequently referred to more succinctly as hexasubstituted hexaazaisowurtzitane derivative.

This novel process is characterized in that the hexanitrohexaazaisowurtzitane is obtained directly, in a single reaction stage, by nitration of the hexasubstituted hexaazaisowurtzitane derivative formed by reaction of the α,β-dicarbonyl derivative with the primary amine.

This process is particularly simple and very inexpensive. It requires only 2 reaction stages to produce the HNIW starting from glyoxal and a primary amine, without a hydrogenolysis stage.

This process is also particularly unexpected.

This is because, according to the present invention, the cyclization of an α,β-dicarbonyl derivative with a carefully chosen primary amine forms a hexaazaisowurtzitane cage, the 6 atoms of which are substituted by groups which can be directly nitrolysed, which is not the case with the benzyl groups in HBIW.

In point of fact, all the attempts described in the state of the art to produce a hexaazaisowurtzitane cage starting from glyoxal and from a primary amine other than benzylamine or from a benzylamine possessing a substituted phenyl ring have proved to be fruitless.

Nielsen et al., in the paper "Polyazapolycyclics by condensation of aldehydes with amines. Formation of 2,4,6,8,10,12-hexabenzyl-2,4,6,8,10,12-hexaazatetracyclo[5.5.0.0$^{5,9}$.0$^{3,11}$]dodecanes from glyoxal and benzylamines", J. Org. Chem., 1990, 55, 1459-1466, mention, for example, that the reaction of amines with glyoxal to form hexaazaisowurtzitane derivatives appears to be limited to benzylamine and to some benzylamines possessing a substituted phenyl ring and that all attempts made starting in particular from heteroarylmethylamines and from allylamines have been fruitless.

Surapaneni and Damavarapu, during the 31st annual international conference of the ICT (Institut Chemische Technologie), Jun. 27-30, 2000 in Karlsruhe (Germany), Energetic Materials, Analysis, Diagnostics and Testing, Process improvements in CL-20 manufacture, pages 108-1 to 108-4, mention, on the one hand, the disadvantages of the need to use benzylamine as starting amine and, on the other hand, that only benzyl amines make it possible to obtain the isowurtzitane backbone, all attempts made with other amines or amides having failed.

The present invention has thus overcome a very deep-rooted preconception established many years ago and then confirmed several times.

According to the present invention, if the starting primary amine is represented by the general formula R—$NH_2$, R being an organic group, the cyclization of this primary amine with an α,β-dicarbonyl derivative forms a 2,4,6,8,10,12-hexaR-2,4,6,8,10,12-hexaazatetracyclo[5.5.0.0$^{5,9}$.0$^{3,11}$] dodecane derivative, that is to say a hexasubstituted hexaazaisowurtzitane derivative, the 6 substituents of which are R groups and the 6 N—R bonds of which can be directly nitrolysed, that is to say the 6 R groups of which are sufficiently electrophilic to be displaced by a nitronium ion when the latter attacks the free pair of the nitrogen atoms, forming an R$^+$ cation which is sufficiently stabilized during this substitution.

Preferably, according to the present invention, the organic group R is chosen from the group consisting of heteroarylmethyl groups and allyl groups, that is to say that the starting primary amine of general formula $RNH_2$ is a heteroarylmethylamine or an allylamine.

Mention may be made, as examples of such amines, of 2-methylaminothiophene, allylamine, 3-methylaminopyridine, 2-methylaminofuran and cinnamylamine.

However, other organic groups are sufficiently electrophilic and suitable in the context of the present invention.

The organic group R can also in particular be an optionally substituted propargyl group, a sulphenyl group, the trimethylsilylethyl group or a naphthylmethyl group, preferably the 1-naphthylmethyl group.

The starting amine can also be an alkylamine or an aliphatic amine comprising one or more releasable groups, for example a methylamine where the methyl group is substituted by an R'—O—, R'—S— or R'—N— group in which R' denotes any organic radical, an acylamine, for example acetamide or propionamide, a haloamine, for example chloramine, a sulphonamide, a phosphoramide, a silylamine or a nitrosamine.

According to the present invention, the α,β-dicarbonyl derivative is preferably glyoxal, whatever its form, in particular in the free, hydrated or polymerized form, or alternatively an oxalic acid derivative, for example an ester or an amide.

Glyoxal is very particularly preferred.

The first stage of reaction of the α,βdicarbonyl derivative with the primary amine which makes it possible to form the hexasubstituted hexaazaisowurtzitane derivative is generally carried out in a polar solvent medium, preferably a mixture of a polar organic solvent and of water. According to a preferred alternative form, the polar organic solvent and the water are miscible in the proportions used. The polar organic solvent/water ratio by weight is preferably between 5 and 20, better still between 6 and 10, when all the reactants are present in the reaction medium.

Mention may be made, as examples of polar organic solvent which can be used, of acetonitrile, alcohols, such as methanol, ethanol and propanol, nitromethane and tetrahydrofuran. Acetonitrile and methanol are particularly preferred, more particularly acetonitrile.

Although the reaction of the α,β-dicarbonyl derivative with the primary amine can take place, but at a slower rate, without catalyst, it is preferable to carry it out in the presence of an acid catalyst of Brönsted acid type or of Lewis acid type.

This catalyst can be an inorganic acid, such as perchloric acid, sulphuric acid, hydrochloric acid or nitric acid, or alternatively an organic acid, such as formic acid or acetic acid. Formic acid is particularly preferred.

It is also possible to use a Lewis acid which is stable in an aqueous medium, such as, in particular, a lanthanide trifluoromethanesulphonate, in particular ytterbium(III) trifluoromethanesulphonate.

Use is preferably made of between 25 mol % and 60 mol % of catalyst with respect to the α,β-dicarbonyl derivative, better still of between 30 mol % and 50 mol %.

Furthermore, although the theoretical stoichiometry of the amine/α,β-dicarbonyl derivative reaction is 2 and although such a ratio can be used, better yields are obtained by using a primary amine/α,β-dicarbonyl derivative molar ratio of between 2.5 and 3.5, for example in the region of 3.

The concentration of primary amine in the reaction medium is preferably between 1 mol/liter and 6 mol/liter.

According to a particularly preferred alternative form, the α,β-dicarbonyl derivative is slowly added to the reaction medium comprising beforehand all the amine, the polar organic solvent and optionally the catalyst.

The temperature of the reaction medium is preferably between 0° C. and 25° C., preferably between 0° C. and 15° C. Better still, it is first of all between 0° C. and 5° C. and then it is gradually increased up to a value of between 15° C. and 25° C.

The duration of the reaction can be variable according to the materials and operating conditions. It is generally between 1 h and 20 h.

The hexasubstituted hexaazaisowurtzitane derivative obtained is subsequently preferably isolated from the reaction medium and then purified according to conventional means, such as filtration, separation by settling, extraction with ether, or purification through silica gel or alumina gel.

The HNIW is subsequently obtained directly, in a single reaction stage, by nitration of this hexasubstituted hexaazaisowurtzitane derivative using a conventional nitrating reagent. Use may in particular be made, as nitrating reagent, of $N_2O_5$, nitronium tetrafluoroborate, concentrated nitric acid, a fuming nitric acid, an acetic acid/nitric acid mixture or a sulphuric acid/nitric acid mixture. Sulphuric acid/nitric acid mixtures are particularly preferred, in particular those having an $HNO_3/H_2SO_4$ ratio by weight of between 0.7 and 4, better still of between 1 and 2.

Without this being necessary, this nitration stage can be carried out in the presence of an organic solvent, in particular a halogenated organic solvent, such as dichloromethane or chloroform.

It is also, preferably, possible to prepare the mixture of the reactants (hexasubstituted hexaazaisowurtzitane derivative and nitrating reagent) in the presence of the organic solvent at a temperature, for example, of between −10° C. and 25° C., to subsequently remove all or part of the solvent and then to continue the nitration reaction at a higher temperature, for example between 45° C. and 85° C.

Generally, according to the present invention, a very large molar excess of nitrating agent with respect to the stoichiometry of the reaction is used.

Hydrolysis of the reaction medium makes it possible subsequently to precipitate the HNIW formed, which can then be isolated and recovered, for example by simple filtration.

Another subject-matter of the present invention is the abovementioned novel intermediate hexasubstituted hexaazaisowurtzitane derivatives formed, isolated and identified, namely the 2,4,6,8,10,12-hexaR-2,4,6,8,10,12- hexaazatetracyclo[5.5.0.0$^{5,9}$.0$^{3,11}$]dodecane derivatives, for which R represents an electrophilic organic group, that is to say sufficiently electrophilic for the 6 N—R bonds to be able to be directly nitrolysed, preferably a heteroarylmethyl group, an allyl group, a propargyl group, the trimethylsilylethyl group, a naphthylmethyl group or a sulphenyl group.

The following nonlimiting examples illustrate the invention and the advantages which it provides.

EXAMPLE 1

Synthesis of 2,4,6,8,10,12-hexa(thiophen-2-ylmethyl)-2,4,6,8,10,12-hexaazatetracyclo-[5.5.0.0$^{5,9}$.0$^{3,11}$]dodecane, also known as hexa(thiophen-2-ylmethyl)isowurtzitane.

The standard formula of the thiophen-2-ylmethyl radical is

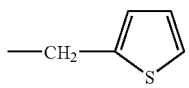

100 ml of acetonitrile, 10 ml of distilled water, 0.093 mol of 2-methylaminothiophene and 0.0093 mol of formic acid are successively introduced into a 250 ml round-bottomed flask equipped with a thermometer which is cooled to between 0° C. and 10° C. with an ice bath. 0.031 mol of glyoxal in the form of a 40% aqueous solution is subsequently run in dropwise (duration approximately 10 min).

The reaction medium is stirred for 18 h while allowing its temperature to return to ambient temperature (approximately 20° C.).

After halting the stirring, a thick gum separates by settling at the bottom of the round-bottomed flask. The supernatant is withdrawn and this gum is dissolved in 40 ml of chloroform.

After drying the chloroform solution over sodium sulphate and then filtering, this solution is concentrated under vacuum. A straw yellow solid contaminated by a viscous oil is recovered, which solid is purified on silica gel using a hexane/diethyl ether eluent mixture in the respective proportions by volume 5/1.

The purified product thus obtained is 2,4,6,8,10,12-hexa(thiophen-2-ylmethyl)-2,4,6,8,10,12-hexaazatetracyclo [5.5.0.0$^{5,9}$.0$^{3,11}$]dodecane, identified by $^1$H NMR and $^{13}$C NMR spectroscopic analyses in CDCl$_3$ and by X-ray crystallography.

The yield of purified product obtained with respect to the glyoxal is 40%.

$^1$H NMR (ppm, CDCl$_3$): δ=3.83, s (2H), cage CH 4.24, s, and 4.35, q (16H), cage CH and CH$_2$ 6.6-7.3, m (18H), aromatic CH $^{13}$C NMR (ppm, CDCl$_3$): δ=51.3, 52.8, CH$_2$ 76.4, 81.6, CH 125.26, 125.37, 125.43, 126.0, 126.9, 127.0, 145.6, 146.1, aromatic C.

The structure of the compound was confirmed by an X-ray determination on a single crystal:
Space group: P21/n
Unit cell parameters: a=12.56799 Å
b=15.82700 Å
c=18.92300 Å
α=90.000°
β=106.320°
γ=90.000°

EXAMPLE 2

Synthesis of 2,4,6,8,10,12-hexacinnamyl-2,4,6,8,10,12-hexaazatetracyclo[5.5.0.0$^{5,9}$.0$^{3,11}$]-dodecane, also known as hexacinnamylisowurtzitane The standard formula of the cinnamyl radical is

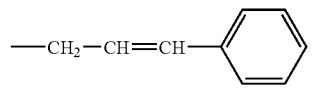

The preparation is carried out according to Example 1 by using, on the one hand, cinnamylamine instead of 2-methylaminothiophene and, on the other hand, a hexane/diethyl ether purification eluent mixture in the respective proportions by volume 5/2 instead of 5/1.

The purified product thus obtained is 2,4,6,8,10,12-hexacinnamyl-2,4,6,8,10,12-hexaazatetracyclo-[5.5.0.0$^{5,9}$.0$^{3,11}$]dodecane, identified by $^1$H NMR and $^{13}$C NMR. The yield of purified product obtained with respect to the glyoxal is 18%.

$^1$H NMR (ppm, CD$_3$COCD$_3$): δ=3.98-4.04, m (12H), allyl CH$_2$ 4.20, s (2H), cage CH 4.46, s (4H), cage CH 6.33-6.79, m (12H), ethylene CH 7.3-7.6, m (30H), aromatic CH $^{13}$C NMR (ppm, CD$_3$COCD$_3$): δ=55.7, 56.4, allylic CH$_2$ 78.2, 82.2, cage CH 127.48, 127.55, 128.27, 128.33, 129.65, 129.77, 130.45, 130.74, 132.43, 132.57, 138.7, 138.8, aromatic C and ethylenic CH.

EXAMPLE 3

Synthesis of 2,4,6,8,10,12-hexa(pyrid-3-ylmethyl)-2,4,6,8,10,12-hexaazatetracyclo-[5.5.0.0$^{5,9}$.0$^{3,11}$]dodecane, also known as hexa(pyrid-3-ylmethyl)isowurtzitane The standard formula of the pyrid-3-ylmethyl radical is

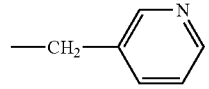

100 ml of acetonitrile, 10 ml of distilled water, 0.093 mol of 3-methylaminopyridine and 0.0093 mol of formic acid are successively introduced into a 250 ml round-bottomed flask equipped with a thermometer which is cooled to between 0° C. and 10° C. with an ice bath.

0.031 mol of glyoxal in the form of a 40% aqueous solution is subsequently run in dropwise (duration approximately 10 min).

The reaction medium is stirred for 18 h while allowing its temperature to return to ambient temperature (approximately 20° C.) and then 150 ml of diethyl ether are added to the reaction medium.

After separation by settling, the organic phase is recovered and is dried over sodium sulphate, then filtered and concentrated under vacuum. The crude product thus obtained is purified on basic alumina deactivated with 6% of water, elution being carried out first with a chloroform/diethyl ether/triethylamine mixture in the respective proportions by volume 5/2/0.1 and then with a chloroform/triethylamine mixture in the respective proportions by volume 5/0.1.

The purified product thus obtained is 2,4,6,8,10,12-hexa(pyrid-3-ylmethyl)-2,4,6,8,10,12-hexaazatetracyclo-[5.5.0.0$^{5,9}$.0$^{3,11}$]dodecane, identified by $^1$H NMR and $^{13}$C NMR.

The yield of purified product obtained with respect to the glyoxal is 19%.

$^1$H NMR (ppm, CD$_3$COCD$_3$): δ=3.89, s (2H), cage CH 4.24-4.58, m (16H), cage CH and CH$_2$ 7.30-8.60, m (24H), aromatic CH $^{13}$C NMR (ppm, CD$_3$COCD$_3$): δ=54.3, 55.1, CH$_2$ 77.1, 81.8, cage CH 124.1, 135.4, 135.6, 136.4, 137.1, 149.3, 150.2, 151.1, aromatic CH.

EXAMPLE 4

Synthesis of 2,4,6,8,10,12-hexaallyl-2,4,6,8,10,12-hexaazatetracyclo[5.5.0.0$^{5,9}$.0$^{3,11}$]-dodecane, also known as hexaallylisowurtzitane 150 ml of acetonitrile, 0.93 mol of allylamine and 0.13 mol of formic acid in 1 g of water are successively introduced into a 250 ml round-bottomed flask equipped with a thermometer which is cooled to between 0° C. and 2° C. with an ice bath.

0.31 mol of glyoxal in the form of a 40% aqueous solution is subsequently run in dropwise (duration approximately 75 min).

The reaction medium is stirred at 0° C. for 45 min and then it is filtered under an argon atmosphere, which makes it possible to directly obtain, without a purification stage, pure 2,4,6,8,10,12-hexaallyl-2,4,6,8,10,12-hexaazatetracyclo[5.5.0.0$^{5,9}$.0$^{3,11}$]-dodecane, identified by $^1$H NMR and $^{13}$C NMR, with a yield of 20% with respect to the glyoxal.

$^1$H NMR (ppm, CDCl$_3$): δ=3.55-3.70, m (12H), allylic CH$_2$ 3.85, s (2H), cage CH 4.16, s (4H), cage CH 5.0-5.3, m (12H), ethylenic CH$_2$ 5.75-6.0, m (6H), ethylenic CH $^{13}$C NMR (ppm, CDCl$_3$): δ=56.4, 56.7, allylic CH$_2$ 77.7, 80.8, cage CH 116.6, 117.6, ethylenic CH$_2$ 137.9, 138.4, ethylenic CH.

EXAMPLE 5

Synthesis of 2,4,6,8,10,12-hexafurfuryl-2,4,6,8,10,12-hexaazatetracyclo[5.5.0.0$^{5,9}$.0$^{3,11}$]-dodecane, also known as hexafurfurylisowurtzitane The standard formula of the furfuryl radical, also known as the 2-furylmethyl radical, is

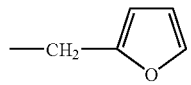

150 ml of acetonitrile, 0.93 mol of 2-aminomethylfuran and 0.13 mol of formic acid in 1 g of water are successively introduced into a 500 ml round-bottomed flask equipped with a thermometer which is cooled to 0° C. with an ice bath.

0.31 mol of glyoxal in the form of a 40% aqueous solution is subsequently run in dropwise (duration approximately 20 min) while maintaining the temperature between 2° C. and 5° C. The temperature is subsequently gradually increased, over 1 h, up to 10° C. and is then gradually increased, over 2 h, up to 15° C. The reaction medium is then stirred at 15° C. for 2 h.

After separation by settling, the heavy phase is collected and concentrated and then the residue obtained is taken up in 1 l of diethyl ether.

After washing this ethereal phase with water (3 times 60 ml), then drying over magnesium sulphate and filtering, the ether is driven off in order to finally collect 2,4,6,8,10,12-hexafurfuryl-2,4,6,8,10,12-hexaazatetracyclo[5.5.0.0$^{5,9}$.0$^{3,11}$]dodecane, identified by $^1$H NMR and $^{13}$C NMR, with a yield of 60% with respect to the glyoxal.

$^1$H NMR (ppm, CDCl$_3$): δ=3.58, s (2H), cage CH 4.05, s (4H), CH$_2$, and 4.09, q (8H), CH$_2$ 4.23, s (4H), cage CH 5.93-6.40, m (12H), aromatic CH 7.35, m (6H), aromatic CH $^{13}$C NMR (ppm, CDCl$_3$): δ=49.2, 50.3, CH$_2$ 77.2, 80.1, cage CH 108.1, 108.4, 110.7, 142.4, 142.5, 154.0, 154.8, aromatic CH.

EXAMPLE 6

Synthesis of 2,4,6,8,10,12-hexapropargyl-2,4,6,8,10,12-hexaazatetracyclo[5.5.0.0$^{5,9}$.0$^{3,11}$]-dodecane, also known as hexapropargylhexaazaisowurtzitane 100 ml of acetonitrile, 10 ml of water, 0.0093 mol of formic acid and 0.093 mol of propargylamine are introduced into a 250 ml two-necked round-bottomed flask cooled to 0~2° C.

0.031 mol of glyoxal in the form of a 40% aqueous solution is subsequently run in dropwise.

The reaction medium is stirred at between 0 and 2° C. for 75 min and then it is concentrated under reduced pressure.

After extracting with dichloromethane and then drying over sodium sulphate, the extraction solvent is evaporated, which makes it possible to obtain a crude product which is purified on basic alumina gel. Finally, 2.11 g of a white solid are obtained, which solid is identified by $^1$H NMR, $^{13}$C NMR, its melting point, elemental analysis and X-ray radiocrystallography as being hexapropargylhexaazaisowurtzitane.

The yield of purified product with respect to the glyoxal is 17%.

Melting point: 114.0° C.-114.3° C. Elemental analysis: C: 71.7% (theory 72.7%) H: 6.2% (theory 6.1%) N: 19.8% (theory 21.2%) $^1$H NMR (ppm, CDCl$_3$): δ=2.21 (t, 4H, J=2 Hz) 2.28 (t, 2H, J=2 Hz) 3.78 (m, 12H) 4.15 (s, 2H) 4.47 (s, 4H) $^{13}$C NMR (ppm, CDCl$_3$): δ=41.1 (CH$_2$) 42.1 (CH$_2$) 71.2, 73.0 (Q) 75.5, 80.7, 80.9, 81.5 (CH).

The analysis by X-ray radiocrystallography from a single crystal obtained by evaporation of a solution of the product in a methanol/ethanol mixture confirms the structure of the product.

EXAMPLE 7

Synthesis of 2,4,6,8,10,12-hexa(parachlorophenylsulphenyl)-2,4,6,8,10,12-hexaazatetracyclo-[5.5.0.0$^{5,9}$.0$^{3,11}$]dodecane, also known as hexa(parachlorophenylsulphenyl)hexaazaisowurtzitane The preparation is carried out according to Example 6, except that the amine employed is parachlorobenzenesulphenamide (instead of propargylamine) and that neither water nor formic acid catalyst is introduced. The structure of the product obtained was characterized by DEPT and $^{13}$C NMR by virtue in particular of the CH (cage) units resonating at 88.3 and 88.8 ppm.

EXAMPLES 8 and 9

Synthesis of 2,4,6,8,10,12-hexa-(1-naphthylmethyl)-2,4,6,8,10,12-hexaazatetracyclo-[5.5.0.0$^{5,9}$.0$^{3,11}$] dodecane, also known as hexa-(1-naphthylmethyl) hexaazaisowurtzitane

EXAMPLE 8

The preparation is carried out according to Example 6, except that the amine employed is 1-naphthylmethylamine (instead of propargylamine) and that the reaction is allowed to take place at ambient temperature (approximately 20° C.) for 36 h.

The yield of purified desired product with respect to the glyoxal is 25%. Its melting point is 244-245° C.

The product was identified as being hexa(1-naphthylmethyl)hexaazaisowurtzitane by $^1$H NMR and $^{13}$C NMR:

$^1$H NMR (ppm, CDCl$_3$): δ=7.3-8.2 (m, 34H) 6.89 (t, 4H) 5.90 (d, 4H) 4.69 (s, 4H) 4.60 (s, 4H) 4.33 (AB, 8H) 3.45 (s, 2H) $^{13}$C NMR (ppm, CDCl$_3$) δ=78.8 (CH) 78.0 (CH) 55.5 (CH$_2$) 53.5 (CH$_2$).

EXAMPLE 9

The preparation is carried out according to Example 8, except that the formic acid is replaced by ytterbium(III) trifluoromethanesulphonate.

The yield of purified hexa(1-naphthylmethyl)hexaazaisowurtzitane obtained with respect to the glyoxal is 62%.

EXAMPLE 10

Synthesis of hexanitrohexaazaisowurtzitane by direct nitration of hexafurfurylisowurtzitane 12 g of 100% nitric acid are introduced, under an argon atmosphere, into a 100 ml round-bottomed flask equipped with a mechanical stirrer, a reflux condenser, a temperature probe and a dropping funnel. The temperature is brought to 10° C. using an ice/salt bath, then 8 g of concentrated sulphuric acid are added and then 10 ml of dry dichloromethane are added.

A solution of 0.0014 mol of hexafurfurylisowurtzitane, obtained according to Example 5, in 5 ml of dichloromethane is subsequently added dropwise (duration approximately 20 min) at a temperature of between −5° C. and −3° C.

The ice/salt bath is then removed in order to allow the temperature to rise up to 10° C.

The dichloromethane is subsequently driven off, while flushing with argon, by bringing the temperature of the reaction medium to 30° C.

The temperature of the reaction medium is subsequently gradually raised, over 4 h, up to 65° C.

After hydrolysis in ice and then filtration, 71.5 mg (12% yield) of a pure solid are recovered, which solid is identified as being hexanitrohexaazaisowurtzitane by $^1$H NMR, $^{13}$C NMR and FTIR spectrometry and by liquid chromatography (HPLC), by comparison of the retention time with an authentic sample.

The Fourier Transform InfraRed (FTIR) spectrum is that of the γ-polymorphic form.

EXAMPLE 11

Synthesis of hexanitrohexaazaisowurtzitane by direct nitration of hexaallylisowurtzitane with nitronium tetrafluoroborate 0.0147 mol of NO$_2$BF$_4$ is introduced, at a temperature of 5° C., into a solution of 0.00254 mol of hexaallylisowurtzitane, synthesized according to Example 4, in 25 ml of dichloromethane.

The medium is subsequently allowed to re-warm up to ambient temperature (approximately 20° C).

The presence of hexanitrohexaazaisowurtzitane is detected in the reaction medium by HPLC.

EXAMPLE 12

Synthesis of hexanitrohexaazaisowurtzitane by direct nitration of hexaallylisowurtzitane with a sulphuric acid/nitric acid mixture 0.00245 mol of hexaallylisowurtzitane, synthesized according to Example 4, is introduced into a mixture, at −5° C., of 0.171 mol of nitric acid and 0.03425 mol of sulphuric acid. The reaction medium is subsequently slowly heated up to 70° C. over 5 hours. A yellow solid, isolated by filtration of the medium, is formed which comprises hexanitrohexaazaisowurtzitane, identified by $^1$H NMR and HPLC.

The invention claimed is:

1. A process for the synthesis of hexanitrohexaazaisowurtzitane, consisting of:
   a) reacting an α,β-dicarbonyl compound with a primary amine to form a hexasubstituted hexaazaisowurtzitane compound, and
   b) nitrating the hexasubstituted hexaazaisowurtzitane compound obtained in step (a) to directly obtain the hexanitrohexaazaisowurtzitane.

2. The process according to claim 1, wherein the α,β-dicarbonyl compound is glyoxal.

3. The process according to claim 1, wherein the primary amine is chosen from the group consisting of heteroarylmethylamines and allylamines; propargylamine; parachlorobenzenesulphenamide and 1-napthylmethylamine.

4. The process according to claim 3, wherein the primary amine is allylamine or 2-aminomethylfuran.

5. The process according to claim 1, wherein the first stage of reaction of an α,β-dicarbonyl compound with a primary amine is carried out in a mixture of a polar organic solvent and water, in the presence of an acid catalyst.

6. The process according to claim 5, wherein the acid catalyst/α,β-dicarbonyl compound molar ratio is between 0.25 and 0.6.

7. The process according to claim 1, wherein the primary amine/α,β-dicarbonyl compound molar ratio is between 2.5 and 3.5.

8. The process according to claim 1, wherein the temperature of the reaction of the primary amine with the α,β-dicarbonyl compound is between 0° C. and 25° C.

9. The process according to claim 1, wherein the hexasubstituted hexaazaisowurtzitane compound formed is isolated from the reaction medium before nitration.

10. The process according to claim 1, wherein the nitration of the hexasubstituted hexaazaisowurtzitane compound is carried out using a sulphuric acid/nitric acid mixture.

11. The process according to claim 1, wherein the nitration of the hexasubstituted hexaazaisowurtzitane compound is carried out in the presence of an organic solvent.

12. The process according to claim 11, wherein during the stage of nitration of the hexasubstituted hexaazaisowurtzitane compound, the reactants are mixed in the presence of the organic solvent at a temperature of between −10° C. and 25° C., all or part of the organic solvent is subsequently removed and then the nitration reaction is continued at a temperature of between 45° C. and 85° C.

13. 2,4,6,8,10,12-hexa R-2,4,6,8,10,12-hexaazatetracylco (5.5.0.05$^{5,9}$.0$^{3,11}$) dodecane compounds, wherein R is chosen from the group consisting of heteroarylmethyl groups, allyl groups, propargyl groups, trimethylsilyethyl groups, naphthylmethyl groups and sulphenyl groups.

* * * * *